United States Patent [19]

Elings et al.

[11] Patent Number: 4,537,861

[45] Date of Patent: Aug. 27, 1985

[54] APPARATUS AND METHOD FOR HOMOGENEOUS IMMUNOASSAY

[76] Inventors: Virgil B. Elings, P.O. Box 6463, Santa Barbara, Calif. 93111; David F. Nicoli, 448 Mills Way, Goleta, Calif. 93017

[21] Appl. No.: 463,658

[22] Filed: Feb. 3, 1983

[51] Int. Cl.³ ................ G01N 33/54; G01N 33/58
[52] U.S. Cl. ................................ 436/518; 356/317; 356/318; 356/417; 436/519; 436/524; 436/525; 436/526; 436/535; 436/805; 436/807
[58] Field of Search ............. 250/461.1, 461.2; 356/317, 318, 417; 436/517, 518, 528, 819, 805, 807

[56] References Cited

U.S. PATENT DOCUMENTS

| | | | |
|---|---|---|---|
| 3,392,282 | 7/1968 | Astheimer | 250/83.3 |
| 3,967,933 | 7/1976 | Etess et al. | 23/232 |
| 3,975,098 | 8/1976 | West | 250/461.1 |
| 4,000,252 | 12/1976 | Kosak | 424/1 |
| 4,020,151 | 4/1977 | Bolz | 436/531 |
| 4,075,481 | 2/1978 | Stoft et al. | 250/343 |
| 4,087,690 | 5/1978 | Prober | 250/343 |
| 4,092,408 | 5/1978 | Litt | 436/531 |
| 4,115,535 | 9/1978 | Giaever | 436/531 |
| 4,153,369 | 5/1979 | Kallet | 250/461.1 |
| 4,177,253 | 12/1979 | Davies | 436/531 |
| 4,197,361 | 4/1980 | Hoff | 436/531 |
| 4,421,860 | 12/1983 | Elings | 356/417 |

OTHER PUBLICATIONS

Wear, 29, (1974), pp. 41–47, "Measurement of Thin Liquid Films by a Fluorescence Technique", Smart, A. E., et al.

Primary Examiner—Sidney Marantz
Assistant Examiner—Stephen C. Wieder
Attorney, Agent, or Firm—Charles H. Schwartz; Ellsworth R. Roston

[57] ABSTRACT

Apparatus and method for an immunoassay of a binding reaction between a ligand and an antiligand which are typically an antigen and an antibody, including a spatial pattern formed by a spatial array of separate regions of antiligand material, and ligand material dispersed to interact with the spatial array of separate regions of antiligand material for producing a binding reaction between the ligand and the antiligand in the spatial patterns and with the bound complexes labeled with a particular physical characteristic. A source of input energy and with the input energy at a particular spectrum for interacting with particular physical characteristic of the labeled binding reaction. Scanning the spatial pattern with the input energy at the particular spectrum for producing output energy having amplitude levels formed by a substantially random background component and a non-random component representing the labeled bound complexes, and the non-random component representing the labeled bound complexes detected to produce an output signal in accordance with the labeled binding reaction.

67 Claims, 11 Drawing Figures

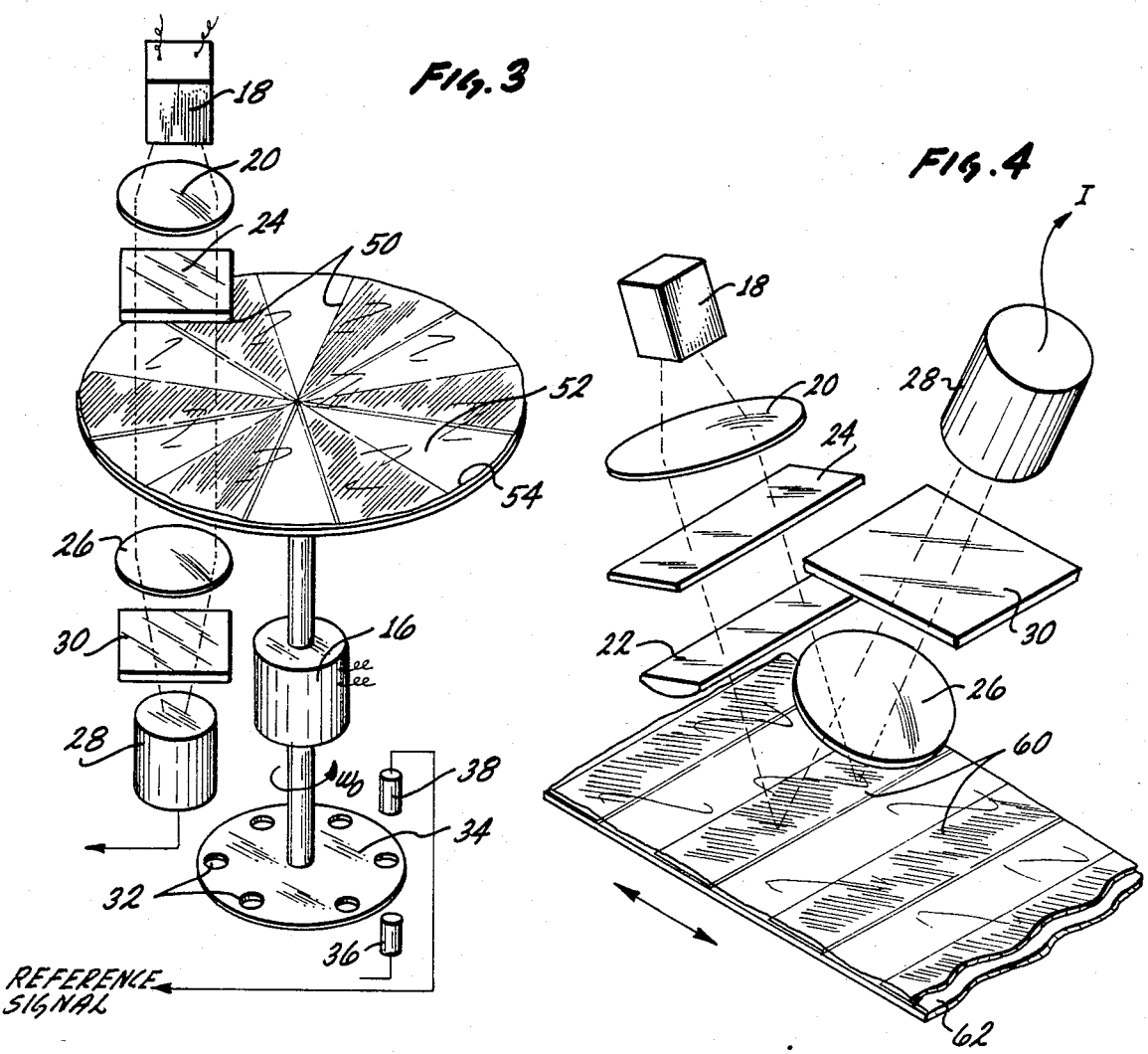
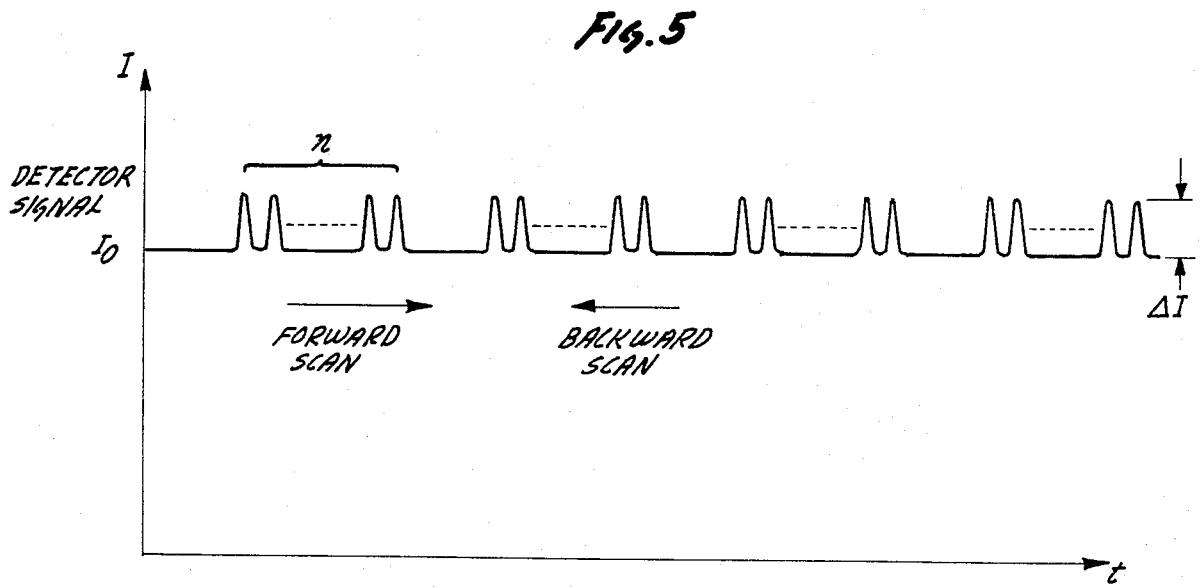

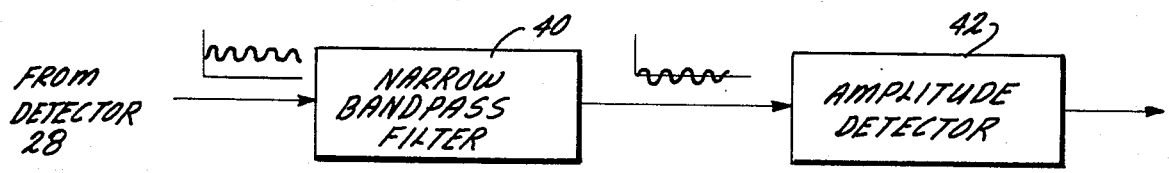
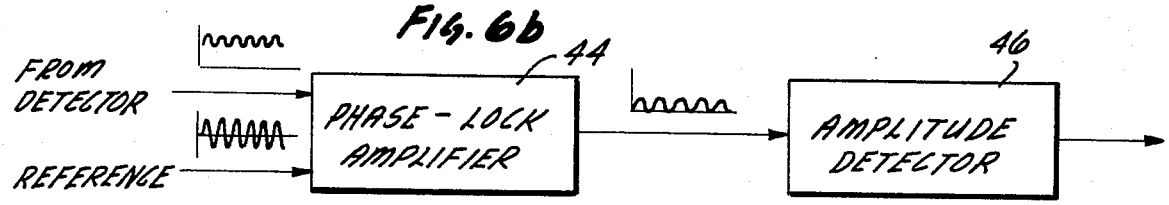
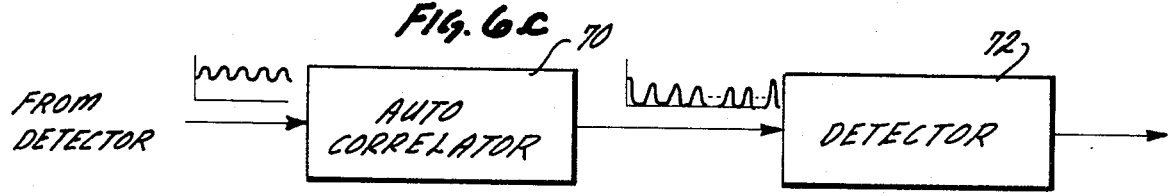
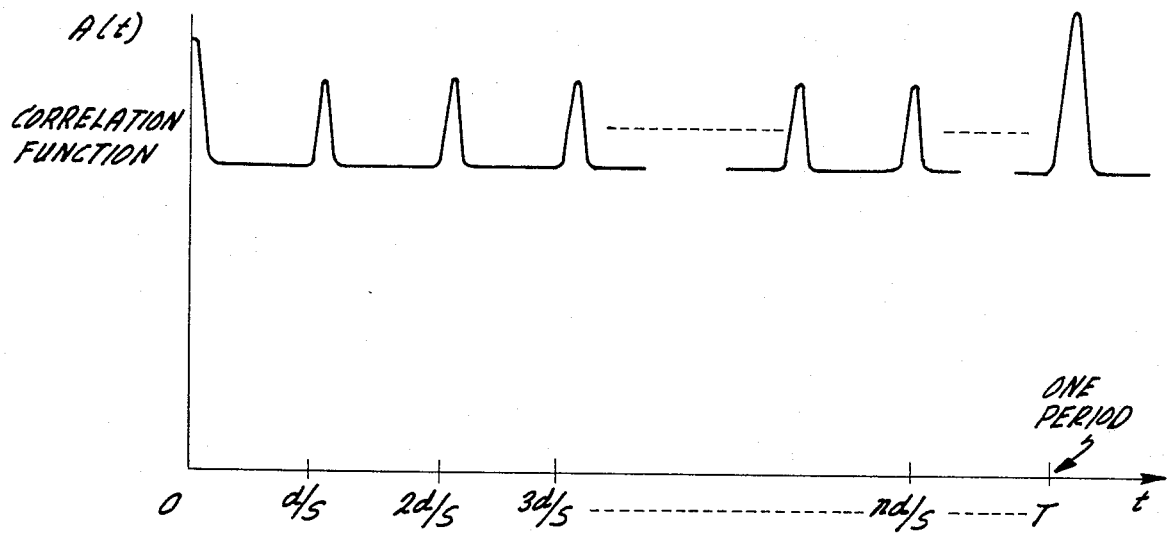

APPARATUS AND METHOD FOR HOMOGENEOUS IMMUNOASSAY

BACKGROUND OF THE INVENTION

1. Field of the Invention

The present invention is directed to a new type of immunoassay, which includes a sensitive technique for the quantitative detection of low concentrations of molecules of a particular type such as molecules in solution.

2. Description of the Prior Art

It is desirable in certain circumstances to measure very low concentrations of certain organic compounds. In medicine, for example, it is very useful to determine the concentration of a given kind of molecule, usually in solution, which either exists naturally in physiological fluids (e.g. blood or urine) or which has been introduced into the living system (e.g. drugs or contaminants). Because of the rapidly advancing state of understanding of the molecular basis of both the normal and diseased states of living systems, there is an increasing need for methods of detection which are quantitative, specific to the molecule of interest, highly sensitive and relatively simple to implement. Examples of molecules of interest in a medical and/or biological context include, but are not limited to, drugs, sex and adrenal hormones, biologically active peptides, circulating hormones and excreted antigens associated with tumors. In the case of drugs, for example, it is often the case that the safe and efficacious use of a particular drug requires that its concentration in the circulatory system be held to within relatively narrow bounds, referred to as the therapeutic range.

One broad approach used to detect the presence of a particular compound, referred to as the analyte, is the immunoassay, in which detection of a given molecular species, referred to generally as the ligand, is accomplished through the use of a second molecular species, often called the antiligand, or the receptor, which specifically binds to the first compound of interest. The presence of the ligand of interest is detected by measuring, or inferring, either directly or indirectly, the extent of binding of ligand to antiligand. The ligand may be either monoepitopic or polyepitopic and is generally defined to be any organic molecule for which there exists another molecule (i.e. the antiligand) which specifically binds to said ligand, owing to the recognition of some portion of said ligand. Examples of ligands include macromolecular antigens and haptens (e.g. drugs). The antiligand, or receptor, is usually an antibody, which either exists naturally or can be prepared artificially. The ligand and antiligand together form a homologous pair. Throughout the text the terms antigen and antibody, which represent typical examples, are used interchangeably with the terms ligand and antiligand, respectively, but such usage does not signify any loss of generality. In some cases, the antibody would be the ligand and the antigen the antiligand, if it was the presence of the antibody that was to be detected.

Implementation of a successful immunoassay requires a detectable signal which is related to the extent of antigen-antibody binding which occurs upon the reaction of the analyte with various assay reagents. Usually that signal is provided for by a label which is conjugated to either the ligand or the antiligand, depending on the mode of operation of the immunoassay. Any label which provides a stable, conveniently detectable signal is an acceptable candidate. Physical or chemical effects which produce detectable signals, and for which suitable labels exist, include radioactivity, fluorescence, chemiluminescence, phosphorescence and enzymatic activity, to name a few.

Broadly speaking, immunoassays fall into two general categories—heterogeneous and homogeneous. In heterogeneous assays, the purpose of the label is simply to establish the location of the molecule to which it is conjugated—i.e. to establish whether the labeled molecule is free in solution or is part of a bound complex. Heterogeneous assays generally function by explicitly separating bound antigen-antibody complexes from the remaining free antigen and/or antibody. A method which is frequently employed consists of attaching one of the members of the homologous pair to a solid surface by covalent binding, physical absorption, or some other means. When antigen-antibody binding occurs, the resulting bound complexes remain attached to this solid surface (composed of any suitably inert material such as plastic, paper, glass, metal, polymer gel, etc.), allowing for separation of free antigen and/or antibody in the surrounding solution by a wash step. A variation on this method consists of using small (typically 0.05 to 20 microns) suspendable particles to provide the solid surface onto which either antigen or antibody is immobilized. Separation is effected by centrifugation of the solution of sample, reagents and suspendable beads at an appropriate speed, resulting in selective sedimentation of the support particles together with the bound complexes.

Notwithstanding the successful application of heterogeneous assay procedures, it is generally desirable to eliminate separation steps, since the latter are time-consuming, labor-intensive and sometimes the source of errors in the signal measurement. Furthermore, the more complicated protocols associated with heterogeneous assays make them less suitable for automated instrumentation of the kind needed for large-scale clinical applications. Consequently, homogeneous assays are more desirable. In the homogeneous format, the signal obtained from the labeled ligand or antiligand is modified, or modulated, in some systematic, recognizable way when ligand-antiligand binding occurs. Consequently, separation of the labeled bound complexes from the free labeled molecules is no longer required.

There exist a number of ways in which immunoassays can be carried out. For clarity a heterogeneous format is assumed, although each approach can be utilized (with varying degrees of success) in a homogeneous format, given a suitable label which is modulated by the binding reaction.

In the competitive mode, the analyte, assumed to be antigen, is allowed to compete with a known concentration of labeled antigen (provided in reagent form in the assay kit) for binding to a limited number of antibody molecules which are attached to a solid matrix. Following an appropriate incubation period, the reacting solution is washed away, ideally leaving just labeled antigen-antibody complexes attached to the binding surface, thereby permitting the signal from the labels to be quantitated.

In another method, called the sandwich mode, the analyte, again assumed to be antigen, reacts with an excess of surface-immobilized antibody molecules. After a suitable incubation period, an excess of label-conjugated antibody is added to the system. After this reaction has gone to essential completion, a wash step removes unbound labeled antibody and other sources of contamination, permitting measurement of the signal produced by labels which are attached to antibody-antigen-antibody complexes.

In yet another approach, called the indirect mode, the analyte, this time assumed to consist of specific antibody, is allowed to bind to surface-immobilized antigen which is in excess. The binding surface is then washed and allowed to react with label-conjugated antibody. After a suitable incubation period the surface is washed again, removing free labeled antibody and permitting measurement of the signal due to labeled antibody. The resulting signal strength varies inversely with the concentration of the starting (unknown) antibody, since labeled antibody can bind only to those immobilized antigen molecules which have not already complexed to the analyte.

One of the most sensitive immunoassays developed thusfar is the radioimmunoassay (RIA), in which the label is a radionuclide, such as $I^{125}$, conjugated to either member of the homologous (binding) pair. This assay, which is necessarily heterogeneous, has achieved extremely high sensitivities, extending down to the vicinity of $10^{-17}$ molar for certain analytes. The obvious advantage of radioactive labeling, and the reason for the extremely high sensitivity of RIA-type assays, is that there exists negligible natural background radioactivity in the samples to be analyzed. Also, RIA is relatively insensitive to variations in the overall chemical composition of the unknown sample solution. However, the radioactive reagents are expensive, possess relatively short shelf lives and require the use of sophisticated, expensive instrumentation as well as elaborate safety measures for both their use and disposal. Hence, there is an increasing motivation to develop non-isotopic assays.

Fluorescence provides a potentially attractive alternative to radioactivity as a suitable label for immunoassays. For example, fluorescein (usually in the form of fluorescein isothiocyanate, or "FITC") and a variety of other fluorescent dye molecules can be attached to most ligands and receptors without significantly impairing their binding properties. Fluorescent molecules have the property that they absorb light over a certain range of wavelengths and (after a delay ranging from $10^{-9}$ to $10^{-4}$ seconds) emit light over a range of longer wavelengths. Hence, through the use of a suitable light source, detector and optics, including excitation and emission filters, the fluorescence intensity originating from labeled molecules can be determined.

Several heterogeneous fluorescence-based immunoassays (FIA) have been developed, including the FIAX/StiQ TM method (IDT Corp., Santa Clara, CA.) and the Fluoromatic TM method (Bio-Rad Corp., Richmond, CA.). In the former case, antigen is immobilized on an absorbant surface consisting of a cellulose-like polymer mounted on the end of a portable "dipstick", which is manually inserted into sample, reagent and wash solutions and ultimately into the fluorescence measuring instrument. A competitive reaction utilizing FITC-labeled monospecific antibody is typically employed. In the Bio-Rad assay kit, the solid surface is replaced by suspendable polyacrylamide gel microbeads which carry covalently-bound specific antibody. A sandwich mode is typically employed, with centrifugal sedimentation, followed by resuspension, of the beads for separation and measurement. Photon-counting techniques can be used to extend the sensitivity of the fluorescence intensity measurement.

Use of an enzyme as a label has produced a variety of useful enzyme immunoassays (EIA), the most popular of which is known as ELISA. In the typical heterogeneous format a sandwich-type reaction is employed, in which the ligand of interest, assumed here to be antigen, binds to surface-immobilized specific antibody and then to an enzyme-antibody conjugate. After suitable incubation, any remaining free enzyme conjugate is eliminated by a wash or centrifugation step. A suitable substrate for the enzyme is then brought into contact with the surface containing the bound complexes. The enzyme-substrate pair is chosen to provide a reaction product which yields a readily detectable signal, such as a color change or a fluorescence emission. The use of an enzyme as a label services to effectively amplify the contribution of a single labeled bound complex to the measured signal, because many substrate molecules can be converted by a single enzyme molecule.

As discussed previously, it is generally desirable to eliminate the separation steps associated with typical heterogeneous assays and, instead, use homogeneous techniques. One of the first homogeneous assays to be developed was the fluorescence polarization immunoassay. Here, the polarization of the emission of the fluorescent dye label is modulated to an extent which depends on the rate of rotational diffusion, or tumbling, of the label in solution. Free labeled molecules which rotate rapidly relative to the lifetime of their excited states emit light of relatively random polarization (assuming a linearly polarized exciting beam, for example). However, when the label becomes attached to a relatively large bound complex, the rate of tumbling becomes relatively slow, resulting in fluorescence emission of substantially linear polarization (i.e. essentially unchanged). Unfortunately, this technique is limited in practice to the detection of low molecular weight ligands, e.g. drugs, whose rate of tumbling is sufficiently rapid to produce a measurable change in fluorescence polarization upon binding to the antiligand. The extent of modulation of the signal, in any case, is quite small.

Another useful fluorescence-based homogeneous technique is the fluorescence excitation transfer immunoassay (FETI), also known simply as fluorescence quenching. Here, two different dye labels, termed the donor and the acceptor, or quencher are used. The pair has the property that when the labels are brought close together, i.e. to within distances characteristic of the dimensions of antigen-antibody complexes, there is nonradiative energy transfer between the electronically excited donor molecule and the acceptor. That is, the acceptor quenches the fluorescence emission of the donor, resulting in a decreased intensity of the latter. In a typical competitive mode, the donor label is attached to the ligand of interest and the acceptor label fixed to the specific antibody. When ligand is present in the unknown sample, some fraction of the acceptor-labeled antibody binds to the free ligand, leaving a fraction of the labeled ligand unquenched and therefore able to emit fluorescence radiation. The intensity of the latter increases with increasing analyte concentration.

The principal drawback of the FETI technique is the requirement that the donor-labeled ligand be relatively pure. Substantial concentrations of labeled impurities produce a large background signal, making detection of a small change due to complexing all the more difficult. Along these lines, U.S. Pat. No. 4,261,968 describes an assay in which the quantum efficiency of a fluorescent label is decreased when the labeled antigen becomes bound to the antibody, resulting in a decrease in the total fluorescence emission of the sample solution.

One of the main factors which limits the sensitivity and reproducibility of all non-isotopic assays to varying degrees is the presence of background false signals. For example, in fluorescence-based assays the use of untreated blood serum may yield relatively high and variable background fluorescence levels due to the presence of proteins, bilirubin and drugs. In addition, there may exist variations in the absolute fluorescence intensity from one sample to the next due to fluorescence from sample cell surfaces, light scattering from impurities in solution, aberrations on optical surfaces, temperature dependent effects, etc. Problems related to impurities are particularly troublesome in homogeneous assays. However, the background false signal contributions are often relatively constant in time for any given sample measurement. Hence, a very useful technique for reducing the background contribution without the necessity of making additional control measurements is to determine the time rate of change of the signal. Such a rate determination in the early stages of the antigen-antibody binding reaction (i.e. when the rate is largest) should, in principle, be independent of the (constant) background level.

In principle, then, the rate determining procedure can be applied to any homogeneous assay technique, with the added advantage that the binding reaction need not be taken to essential completion, thereby resulting in a faster assay measurement. However, this approach becomes less feasible or advantageous the smaller the total signal change due to binding, relative to the background level. Hence, there are invariably practical limitations to the sensitivity which can be achieved using any of the existing homogeneous non-isotopic immunoassays, given the typical courses of background false signals, interferences and nonspecific effects.

SUMMARY OF THE INVENTION

The present invention is directed to an immunoassay technique in which the contributions to the measured signal due to free labeled ligand or antiligand as well as contaminants and other sources of "background" signal are effectively suppressed, thereby permitting measurement of the desired signal due to labeled bound molecules at very low concentrations. The resulting assay, therefore, possesses a higher sensitivity than those currently in use. This requirement of insensitivity to free labeled molecules plus background contamination holds regardless of the type of labeling and/or detection scheme employed.

The underlying principle of the present invention is that labeled bound ligand-antiligand complexes are caused to reside preferentially in a predetermined spatial pattern. The useful signal due to these labels therefore is forced to exist at or be associated with only certain predetermined locations within the sample solution volume or on a surface. This behavior is in sharp contrast to the origin of the signal due to unbound labeled ligand or labeled antiligand molecules as well as background contamination sources of signal which can be expected to be spatially random. The spatial pattern is scanned spatially while the antigen-antibody binding reaction is proceeding or, if desired, after the reaction has run to completion. Using signal enhancement techniques such as filtering, phase-sensitive detection or autocorrelation, the desired signal level can be greatly enhanced with respect to the contribution from free labeled molecules and background contamination sources, thereby yielding a more sensitive assay. It is to be appreciated that the present invention is not limited to homogeneous assays although such homogeneous assays are desirable. Also, the general principle of having the bound complexes reside in a known spatial pattern is not limited to the use of fluorescent labels. The detected signal can be related, for example, to changes in optical density (either at a specific wavelength or over a broad range of wavelengths), light scattering, color, reflectance, birefringence, magnetism or any other physical variable which can be detected with suitable sensitivity and spatial resolution.

The present invention may be accomplished with a number of different embodiments, but the common principle in each case is to force the bound complexes produced by the ligand-antiligand reaction to occur predominantly in a predetermined spatial (or geometric) pattern and then to scan the region in space with a suitable detector where this pattern is expected to be located and, using noise reduction techniques, to measure the signal due to the binding reaction and effectively suppress the contribution due to free labeled molecules plus background contaminants, which display no such spatial pattern. For example, if the analyte consists of antigen, and labeled antigen is employed in a competitive-type assay, specific antibody can be attached to a solid surface in the form of a spatially periodic array of stripes of predetermined width and spacing. After completion of a competitive reaction as described above, labeled bound antigen will be found only on the antibody-coated stripes, while free labeled antigen and other signal-producing interfering contaminants will in general exist throughout the sample space with more-or-less equal density when there is free diffusion and adequate mixing of all unbound species prior to completion of the binding reaction. Therefore, the signal due to the particular label used will be enhanced at the locations of the antibody-coated stripes.

BRIEF DESCRIPTION OF THE DRAWINGS

A clearer understanding of the invention will be had with reference to the following description and drawings wherein;

FIG. 3 is a second embodiment of the invention;

FIG. 4 is a third embodiment of the invention;

FIG. 5 illustrates the output waveform from the embodiment of FIG. 4;

FIGS. 6(a), 6(b) and 6(c) illustrate three alternate methods of providing an output signal representative of the periodic signal;

FIG. 7 illustrates a waveform representative of a correlation function provided by the method shown in FIG. 6(c)

DESCRIPTION OF THE PREFERRED EMBODIMENTS

Figure 1:
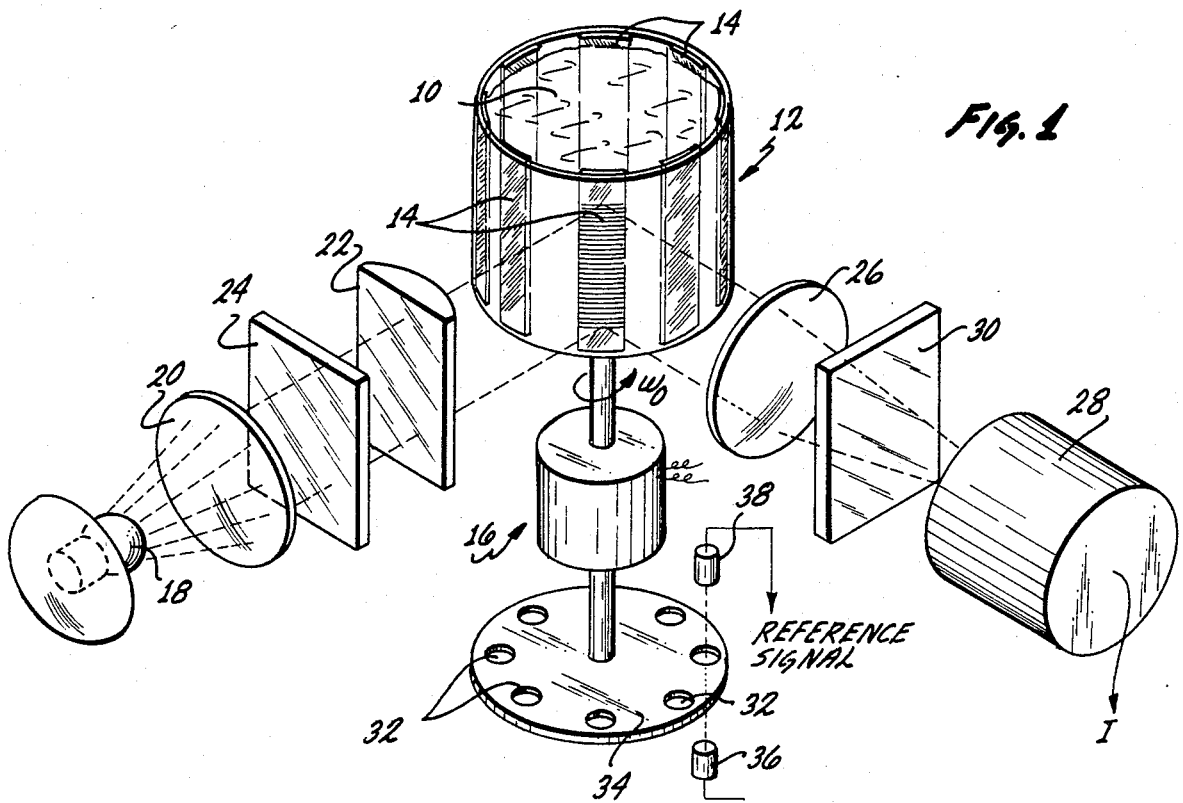
FIG. 1 is a first embodiment of the invention.

A sample solution 10 is contained in a transparent cylindrical glass or plastic tube 12. For the purpose of describing this particular embodiment, it is assumed that the analyte to be measured consists of antigen and that a competitive mode assay is employed. The inside surface of the tube 12 is coated with specific antibody in the form of a ribbed pattern of stripes 14. Typically, the stripes 14 of antibody coating are of equal width and with the spacing between adjacent stripes equal to the width of the stripes, so that, half the inner tube surface is coated with antibody. The tube 12 is rotated by a motor 16 at a constant angular speed $\omega_o$, equivalent to $f_o$ revolutions/sec, where $f_o=\omega o/2\pi$. The tube 12 is illuminated by an exciting light source such as, blue light of wavelength $\lambda=485$ nm in the case of fluorescein labeled molecules. The exciting light consists of a narrow, flat ribbon of light and may be produced using a broad spectrum light source 18 and with the light energy from the light source 18 directed through a collimating lens 20 and a cylindrical lens 22 to have the plane of the focused beam aligned parallel to the stripes on the rotating tube 12 and focused on the surface of the tube. A filter 24 is used to remove all wavelengths but those in a range suitable for excitation of the fluorescent labels. The focused beam excites any fluorescently labeled molecules or impurities which lie in the path of the beam within the sample tube 12. The exciting beam should ideally possess a width which is matched to the width of the antibody-coated stripes 14 but the width of the beam should not exceed the width of the stripes.

An imaging lens 26 is placed close to the rotating tube to collect a fraction of the resulting fluorescence emission and to image the emission onto a detector such as a photo-multiplier tube 28 so as to produce a detected fluorescent signal I. Although other types of detectors such as solid-state photovoltic detectors may be employed, a photo-multiplier tube would typically be used for the most sensitive assay. A filter 30 is used to eliminate light at the exciting wavelength which reaches the detector 28 due to stray reflections from the sample tube 12 and/or scattering from surface imperfections and particles in the solution 10. The desired fluorescent signal is at a longer wavelength than the exciting light.

There are two kinds of contributions to the resulting detected fluorescent signal I. First, there is a signal of magnitude $I_o$, consisting of background fluorescence from the glass tube 12 plus impurities in the sample solution as well as unbound labeled antigen (assuming, for example, a competitive-type assay). In general these background fluorescent sources are expected to be randomly distributed throughout the tube volume, so that the resulting signal bears no systematic relationship to the angular orientation of the tube 12 and there is no characteristic frequency component or phase in this background signal contribution. Second, there is a desired signal of magnitude $\Delta I$ due to labeled antigen which has become bound to the fixed antibody pattern. This contribution of magnitude $\Delta I$ consists of a periodically varying signal of known frequency f, given by $f=nf_o$, where n is the number of antibody-coated stripes 14 located on the inner tube surface. The phase of this bound-label oscillating signal of magnitude $\Delta I$ may be determined with respect to an oscillating reference signal of the same frequency, which can be derived from the rotation of the tube 12. For example, the reference signal may be derived from a pattern of spots or holes 32 of the same periodicity as the antibody stripes 14 located on a disc 34 attached to the rotor shaft of the motor 16. The reference signal may be obtained by an interrupted light beam from a light source 36 and detected by a photo-detector 38. Other simple techniques, such as a magnetic-field-actuated switch may also be used to produce a reference signal.

Figure 2:
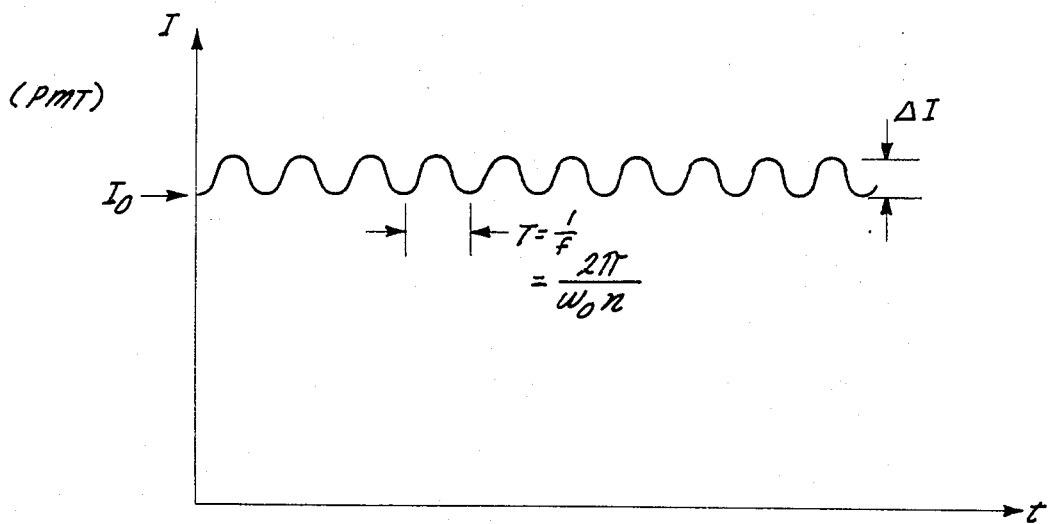
FIG. 2 illustrates the output waveform from the embodiment of FIG. 1.

The detected signal, I, from the photo-multiplier detector 28 is ideally as shown in FIG. 2. As can be seen in FIG. 2 the total detectable fluorescence signal I has been converted into the sum of two components: a periodic waveform of frequency f and magnitude $\Delta I$ due to the bound complexed labeled antigen, superimposed on a background level of intensity $I_o$ which has been represented as a constant. Regardless of the detailed shape of the periodic component, which depends on the precise relationship between the exciting beam size and the stripe width, plus other factors, the desired signal of magnitude $\Delta I$ contains a strong Fourier component at the fundamental frequency f. Of course, in reality there is a certain amount of random and/or systematic "noise" superimposed on the ideal signal shown in FIG. 2 as will be discussed below.

A simple method of extracting the desired signal of magnitude $\Delta I$ consists of passing the output signal from the photo-multiplier 28 through a narrow-frequency bandpass filter 40 as shown in FIG. 6(a). The filter 40 is centered at frequency f, and the peak-to-peak amplitude $\Delta I$ or the root-mean-square (R.M.S.) amplitude may then be measured by an amplitude detector 42 to provide an output signal representative of the oscillating component of the total detected signal. This method effectively blocks the large D.C. component of the signal, $I_o$, due to unbound labeled antigen plus the remaining background fluorescence. In situations where the signal from the pattern is weak due to a low density of labeled bound complexes, the oscillating component may be difficult to measure using a bandpass filter due to the presence of one or more of the following sources of fluctuations (i.e., "noise") in the system which may get through the filter:

(1) Fluctuations in the exciting beam intensity.
(2) Shot noise in the photo-multiplier detector. The fluorescent light consists of discrete photons and therefore has random noise associated with it.
(3) Imperfections in the glass tube surface and/or non-uniformities in antibody coating.
(4) Fluorescent impurity "spots" fixed to the surface of the tube, whose brightness may be comparable to or exceed that of the labeled antigen attached to the antibody-coated stripes.

A more powerful method of extracting the periodic oscillating signal component from the total fluorescence signal is the technique of phase-sensitive detection, using a "lock-in" or phase-lock amplifier 44 shown in FIG. 6(b). Lock-in amplifiers are frequently used for extracting periodic signals, of fixed frequency and phase, from large backgrounds which are random in time. Such amplifiers are available in a sophisticated form from Princeton Applied Research, Princeton, N.J. Simple lock-in amplifiers can be made with a few integrated circuits, for instance, using the GAP-01 Analog Processing Subsystem made by Precision Monolithics, Inc., Santa Clara, CA. The basic idea of a lock-in amplifier is to alternate the polarity of the input signal with a reference signal and then average the resultant signal.

For signals which are not in phase with the reference signal, such as background fluorescence, the average of the output will be zero since half the time the output signal will be positive and half the time negative. For a periodic signal such as a sine wave in phase with the reference signal the average of the output will not be zero. For instance if when the input periodic signal is positive the polarity is not reversed but when the input is negative the input polarity is reversed by the reference signal, the output will always be positive, and the average of this periodic signal will be non-zero.

The phase-lock amplifier 44 therefore can selectively amplify that portion of the input signal which possesses a Fourier component at the fundamental modulation frequency (equal to f in the present case) and whose phase is fixed with respect to a reference signal of the same frequency such as the reference signal produced from the detector 38. In this way, a relatively weak signal at the fundamental frequency can be detected by an amplitude detector 46 from masking noise sources whose r.m.s. amplitudes exceed the desired signal amplitude by as much as several orders of magnitude. The important distinction is that the phases of the Fourier components of the noisy background contribution are random with respect to the periodic reference signal from the detector 38.

Fluctuations (1) and (2) defined above, occur randomly in time, or with respect to the pattern period, and therefore can be largely suppressed using a phase-lock amplifier 44. Fluctuations (3) and (4) defined above, can in principle be reduced by making the system (i.e., glass tube 12, antibody coatings 14, etc.) as uniform as possible and by designing a pattern which is less sensitive to single or only occasional imperfections. Computer techniques also may be used in conjunction with phase-sensitive detection to recognize and reject a given stripe 14 whenever the stripe produces an anomalously large signal contribution which the computer determines is due to a major imperfection. The influence of a particular stripe on the resulting output signal may thereby be minimized.

As described above, the assay can be performed in a non-competitive mode, as in the "sandwich" assay. The sandwich assay can employ the same pattern consisting of surface-immobilized antibody shown in the embodiment of FIG. 1. The unknown sample 10 containing the antigen of interest is put into the tube 12 and allowed to react with the antibody-coated stripes 14. After a suitable incubation period to allow for essential completion of the binding reaction an excess of fluorescently-labeled antibody is then added to the sample solution 10. Assuming that the antigen possesses at least two active binding sites, the antigen can indirectly bind labeled antibody to the surface-immobilized antibody, resulting in antibody-antigen-antibody complexes. As the binding reaction proceeds a fluorescent pattern begins to develop on the pattern of antibody stripes 14. With the sandwich assay, the intensity of fluorescence emission associated with the pattern is ideally directly proportional to the number of antigen molecules in the sample. It is presumed that the number of antibody molecules attached to the tube surface in the form of a pattern substantially exceeds the maximum number of antigen molecules in the sample, so that essentially all of the latter become bound to the surface. The narrow filter 40 or a phase-lock amplifier 44 can be used to extract the amplitude $\Delta I$ of the periodic signal corresponding to the pattern.

In both the competitive and sandwich assays, the labeled ligand usually carries only a single fluorescent label molecule. For this case the binding of one labeled antigen or antibody molecule adds only one fluorescent molecule to the pattern, which increments the measured signal by an exceedingly small amount. The tagging could be performed by coating a tagged "carrier" particle with the antigen or antibody to be tagged. For instance in the "sandwich" mode assay the labeled antibody may be added to the system in the form of fluorescent "carrier" particles which are coated with antibody. These particles may be composed of a suitable inert material such as polystyrene, polyacrylamide gel, etc., which has been impregnated with fluorescent dye molecules such as by covalent binding, hydrophobic association, etc. Antibody may be attached to the outer surface of the particles by covalent binding, physical absorption, etc. The size of these particles would typically be submicron. The fluorescent carrier particles offer the advantage that they produce a fluorescent signal having a much greater amplitude than that obtained from a single fluorescent label molecule. The signal produced by the fluorescent carrier particles may be thousands of times larger depending on the number of fluorescent molecules which are attached to each carrier particle. Therefore, a single binding event increases the fluorescent intensity of one segment of the pattern by a much larger amount than would be the case using ordinary labeled antibody. In effect, the use of carrier particles provides additional amplification for the pattern technique. This amplification becomes important if the assay is to be highly sensitive so as to detect extremely low levels of antigen.

If carrier particles are used in this way to amplify the effect of labeling, the pattern technique can also be used as an alternative to the well-known slide test, based on particle agglutination. A popular qualitative method for performing an assay uses carrier particles (typically latex, submicron) coated with specific antibody. The antigen in the unknown sample binds to the antibody, thereby crosslinking various numbers of carrier particles into aggregates of various sizes. If the agglutination proceeds far enough, representing that the antigen is present in sufficiently large concentration, the aggregates scatter enough light, given a carrier particle diameter of a fraction of a micron or larger, to be detectable with the unaided eye. The resulting degree of flocculation of the typically concentrated carrier particles provides a qualitative indication of the presence of the antigen above a certain concentration. For example, the pregnancy assay (hCG) is usually performed in this way.

An improved visual agglutination assay can be designed by attaching specific antibody to a solid surface in the form of a macroscopic spatial pattern which is easily recognizable by the naked eye (i.e. any simple geometric design, including an alphabet letter, number, etc.). As in the simple slide test, a certain amount of antibody-coated carrier particles in solution is used in contact with the antibody-coated surface. Upon addition of antigen (unknown) and agitation of the solution in contact with the surface, some of the carrier particles begin to bind to the surface-immobilized antibody pattern. To the extent that this preferential positioning of some of the particles (and particle aggregates) on the pattern causes a visually discernable change in color, optical density, reflectance, light scattering or any other optical property, the pattern begins to "stand out" amidst the more-or-less random positioning of all the remaining particles. For example, strongly fluorescing carrier particles can be used. Of course, the antigen also induces some aggregation of free particles in solution which remain unbound to the pattern. The resulting contrast of the pattern with respect to the surrounding solution then depends on the extent of binding to the pattern, the strength of the "signal" caused by the particles, the ratio of the amount of particle-coated antibody to pattern antibody, and other factors.

Although the present invention has been described above with reference to the pattern technique using fluorescence as the signal-producing label to be detected, it is clear that a variety of other physical quantities can be employed as the detectable label variable. One example is optical density. For example, one can employ carrier particles which are relatively opaque (or semi-opaque) to white light or to light of a given wavelength. Again, taking the example in which the unknown analyte is antigen and the carrier particles are coated with antibody, as the antigen-antibody binding reaction progresses the antibody-coated stripes in the pattern will become steadily more optically dense, transmitting less light over the course of the reaction. The signal can be obtained by a simple measurement of transmitted intensity through the pattern segments. In this case, however, another embodiment of the present invention might be preferred, which embodiment is shown in FIG. 3.

The principal difference between the embodiments of FIGS. 1 and 3 is that the pattern now consists of radial stripes 50, or segments, fixed on a circular disc 52. The sample solution exists as a layer 54 of liquid on the disc surface. The disc 52 may be rotated by the motor 16 and with the light source 18. Collimating lens 20 and filter 24 provides for light energy directed to the stripes 50 on the disc 52. If the measurement is of optical density, the filter 24 is optional. The output signal is detected by the imaging lens 26, the filter 30 and the photo-multiplier tube 28. Again, if optical density is being measured, the filter 30 is optional. A phase-lock detection scheme, as shown in FIG. 6(b), may be used to obtain the effective modulation amplitude of the periodic signal, proportional to the concentration of optically dense particles attached to the pattern. Alternatively, the filter system of FIG. 6(a) may be used to provide a measurement of the periodic signal.

Another suitable label, related to optical density, is color. Colored dye molecules can be attached to the antigen, for example, in the case of a competitive assay, or to the excess specific antibody, in the case of a sandwich assay and the dye molecules can be detected by a color change. Colored carrier particles may be used to enhance the change in color which occurs due to binding to the pattern as described above for optical density. As another example, red blood cells can be used to bind to the pattern via the antigenic sites on their membrane outer surfaces. A measurement of the optical density at an appropriate wavelength would provide a sensitive test of the degree of binding of the red cells to the pattern. Of course, other kinds of cells can be used for the same purpose, to detect the presence of certain molecules on their surfaces, provided that there results some detectable change in color, turbidity, etc.

Another physical quantity which may be measured is reflected light. Here, for example, the carrier particles can be metallic particles (e.g. colloidal gold) coated with antibody. As the binding progresses, the reflection of light from the rotating pattern design increases, giving a measure of the amount of antigen-antibody binding and hence the amount of antigen in the sample. In all of these above described measurements the rate at which the pattern appears may be measured. It is important to appreciate that in all of the pattern-related measurements described earlier, as well as those to be described below, the magnitude of the fluctuating component of the signal produced by pattern-bound labels, $\Delta I$, is obtained continuously in time. It obviously increases as more labeled molecules become fixed to the pattern. Hence, in every case one has a homogeneous technique in which the time rate of change of pattern-associated label binding can be obtained. As pointed out in the Background of the Invention, such a rate measurement is highly desirable, in that it provides additional discrimination over background sources of false signal, which are usually approximately constant in time. As well, rate determination generally permits a shorter overall measurement time, in that it does not require that the binding reaction go to essential completion in order to measure the total signal change associated with complete binding.

In all embodiments of the invention, the pattern caused by binding can be formed either by a spatial rearrangement of the labeled molecules or by a modulation of the strength of the label at the binding sites on the pattern. In the first case it is important that all molecules comprising the analyte, as well as all other compounds provided for as reagents, labeled or otherwise, be able to come into efficient contact with each of the antibody or antigen-coated segments which comprise the spatial pattern. In the second case this "mixing" is not needed but one could use a label whose strength is modulated when the binding occurs. A fluorescent label which is quenched upon binding is an example of such a label. Here the fluorescent pattern can form not because of a spatial rearrangement of the labels but because the strengths of the labels on the unbound molecules will be different than the strengths of the labels on the molecules bound to the pattern. This second case could be used where the pattern is on a porous medium and the labeled molecules do not have an opportunity to move about over dimensions comparable to the characteristic size of the pattern and, therefore their concentration remains essentially uniform spatially.

A third embodiment of the pattern technique of the present invention is shown in FIG. 4. In the embodiment of FIG. 4, the antibody coating takes the form of a set of n parallel stripes 60 on a surface 62. For convenience it is assumed that the stripes 60 are of equal width w, with a constant spacing d between centers, where d is greater than w but not necessarily equal to 2w. An output signal due to labeled molecules which are attached to the pattern may be detected by scanning a light beam across the surface while keeping the sample surface stationary or vice versa. As in the first embodiment, a flat ribbon-like beam of light can be created by using the cylindrical focusing lens 22 or by using an opaque mask with a slit aperture. If fluorescence labeling is used to tag either the antigen or antibody, depending on the mode of the assay, then the filter 24 is used to yield a beam whose wavelength range is appropriate to excite the fluorescent tags. The detection is accomplished using the imaging lens 26 and the filter 30 to pass light at the appropriate wavelength to the detector. Bifurcated fiber optics may also be used to advantage to conduct the exciting and fluroscent light to and from the pattern respectively.

The surface 62 could be made of a porous material such as paper. If a porous material were used, the sample solution would absorb into the material and the diffusion of molecular species in the solution would be limited. In this case the tagging of the reaction could be done, for example, with fluorescence quenching so that binding of the tagged molecule would give less fluorescence at the stripes than between stripes even though diffusion were limited.

One method of examining the pattern consists of scanning the light beam back and forth across the array of stripes 60 and specifically along a direction perpendicular to the stripe length and parallel to the pattern surface, with a constant linear speed s in each direction. The scanning amplitude is assumed to be larger than the overall width of the array of stripes so that the detected fluorescence intensity I resembles the waveform of FIG. 5.

The phase-lock amplifier 44 of FIG. 6(b) may be used to extract the pattern signal, from the embodiment of FIG. 4, but this would require a second reference pattern having the same periodicity as that of the antibody pattern. Furthermore, the beam sweep amplitude and alignment with respect to the pattern would in general have to be adjusted carefully to avoid noise artifacts due to loss of phase-lock at the turn-around points of the sweep. The filter method of FIG. 6(a) would also present difficulties to the extraction of the pattern signal due to these turn-around artifacts. As a third alternative, an autocorrelation technique may be used as shown in FIG. 6(c). The technique of autocorrelation is a powerful method for extracting a periodic signal superimposed on a non-periodic background without the need for a reference signal.

The autocorrelation function, A(t), is given by $$A(t) = <I(t') \cdot I(t' \pm T)>$$

where I (t') represents the signal strength (i.e. intensity) detected at time t' and the brackets $<>$ t' denote an integration, or running sum in the case of discrete sampling of the intensity, over times t'. In the example chosen of fluorescense labeling, I(t') represents the fluorescense intensity at time t'. In the case of a reciprocating scan of constant speed s and a uniform spacing d between adjacent stripes 60 (n in number), A (t) resembles the plot of FIG. 7.

The correlation function A(t) produced by an autocorrelator 70 basically possesses a series of peaks of spacing d/s in time, plus a peak at t=0 and one at the scan period T, plus multiples of T, superimposed on a baseline which is closely related to the square of the average fluorescent intensity obtained from the sample. The actual A(t) obtained differs somewhat because of differing relative peak heights, existence of extra peaks etc, from the ideal plot of FIG. 7, depending on the relationship between the beam sweep amplitude and the pattern array size as well as the pattern alignment. Nevertheless, from one or more of the peak heights at t=d/s, 2d/s, ...., nd/s, and the size of the baseline the pattern intensity, independent of the background intensity, can be determined by a detector 72. The peaks in A(t) in FIG. 7 are due to correlations of higher signal intensity corresponding to spacings d, 2d, ...., nd. It is to be appreciated that the autocorrelation technique of FIG. 6(c) also may be used with the first and second embodiments of FIGS. 1 and 3. Whether the phase-lock amplifier or autocorrelator proves to be the superior method of signal detection will depend on the particular design of the apparatus, the detailed nature and strength of the background false signals and the strength of the signal due to pattern-associated labels.

This invention based on binding in a spatial pattern in principle permits multiple homogeneous assays to be performed on the same sample. As a first example several patterns may be located in close proximity on a given surface. Each of the patterns would carry a different antibody, specific to each antigen of interest. The patterns would be distinguishable by having, for example, different periodicities such as, different stripe separations d for the embodiment of FIG. 4. The different patterns are discriminated between by searching for different fundamental frequencies using the phase-lock detector or different correlation peak times using the autocorrelator.

As a second example, the same pattern may be used for each of several assays, but with a different identifying label for each test. This could consist of a different fluorescent wavelength, a different color carrier particle, etc. By using different optical filters a measurement can be made of each pattern intensity either simultaneously, using multiple sets of detecting apparatus, or sequentially using a single basic apparatus.

It should also be appreciated that a variety of scanning schemes may be employed other than the ones already discussed. These include the use of computer-controlled stepping motors to accurately position a scanning beam or sample location representing either rotation or linear displacement, as well as different ilumination/collection schemes, including the use of fiber optics. For example, an optic fiber or fiber bundle can be used to both illuminate a portion of the pattern and detect the fluorescence. Reticles or masks, either stationary or moving, may be used to advantage in conjunction with other optical elements to effectively provide for the scanning of the spatial pattern in a manner which minimizes the need for exacting alignment procedures. One could focus the pattern on a TV camera and scan the pattern electronically.

The existence of substantial numbers of unbound labeled molecules in the assay solution increases the background signal level (e.g. $I_o$ in FIG. 2), regardless of the nature of the label. In principle, however, the existence of a large background, or baseline, level does not influence the measurement of the magnitude of the oscillating signal component associated with the spatial pattern (e.g. $\Delta I$ in FIG. 2), since the background signal due to freely-diffusing labeled molecules is unrelated in frequency or phase to the pattern. On the other hand, fluctuations in the measured signal associated with imperfections in the antibody coating of the pattern or in interposed optical surfaces necessarily remain fixed in phase and frequency and become "locked in" to the spatial pattern, thereby contributing to the apparent signal due to pattern-associated labels. In this case, the use of labeled carrier particles to increase the signal strength associated with the pattern, as discussed above, serves to proportionately reduce the effect of these imperfections. The existence of these non-random fluctuations which are physically fixed with respect to the pattern establishes a practical limit to the ultimate sensitivity which can be achieved by the spatial pattern technique of the present invention, since it is difficult in practice to separate their contribution from that of the desired pattern signal.

False signals associated with imperfections in the surface on which the pattern is located, or of the pattern coating itself, will not change during the assay measurement, so a determination of the rate of change of the signal due to antigen-antibody binding to the pattern allows for the effective removal of these unwanted signals. Also, as indicated above, the phase-lock detector or autocorrelator may be designed (perhaps in conjunction with a computer) to measure the signal due to each segment of the pattern and effectively to ignore those segments which yield an abnormally large or small signal, since such a large deviation in signal is probably due to an imperfection in the pattern surface, optical surface or pattern coating.

All of the embodiments discussed thusfar provide for different means for determining the signal due to labeled molecules which become attached to segments of a spatial pattern as a consequence of antigen-antibody binding reactions. All of these embodiments share one common feature—each requires the existence of a surface onto which a particular spatial pattern of antibody or antigen has been fixed. However, the design of a homogeneous immunoassay based on the detection of binding to a spatial pattern need not be confined to embodiments in which the binding of labeled molecules must occur on a surface. Instead, the pattern may consist of a predetermined, preferential spatial localization of labeled bound complexes which occurs within the bulk volume of the assay solution, requiring no active surface. All that is required for this modification is a means for causing the labeled complexes to seek a set of locations or regions within the solution due to the application of a particular external force field, with the remaining unbound labeled molecules unaffected by that field and hence randomly located throughout the solution. Once this localization of bound labels has been achieved, the signal from the resulting three-dimensional pattern of labels can be readily detected using one or more of the methods described above in connection with the first three embodiments (e.g. filtering, phase-lock detection and autocorrelation).

Figure 8A:
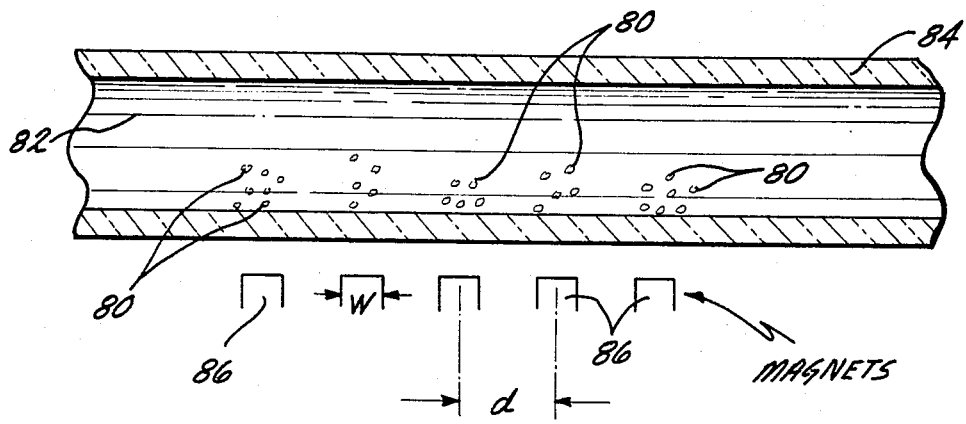
FIG. 8(a) and 8(b) illustrates alternate forms of a fourth embodiment of the invention.

One such external force field which can be utilized is a magnetic field such as shown in FIG. 8(a). The magnetic susceptibilities of typical macro-molecules are prohibitively small. To magnify the forces produced by applying an external magnetic field to the system, one may use small magnetic carrier particles 80 which are designed to form stable suspensions in a sample solution 82 contained in a sample cell 84 and which particles can be coated with antibody or antigen. The size of the particles 80 would typically lie in the range 0.01 to 50 microns. For the purpose of describing the magnetic-field-induced pattern method, a competitive-type assay with fluorescence labeling is assumed, where the analyte consists of antigen. The magnetic carrier particles 80 are coated with specific antibody (by covalent binding, physical absorption, etc.). After the analyte, labeled antigen (of known concentration) and antibody-coated magnetic particles have been introduced into the assay cell volume, a particular magnetic field is applied to the volume—for example, a spatially periodic field resembling a set of "fingers" of high field strength, characterized by an approximate width w and center-to-center spacing d, as illustrated in FIG. 8(a). Such a magnetic field pattern can be formed by using a set of magnets 6 which may be permanent magnets or a series of electromagnets, appropriately spaced. In addition, a material of high permeability may be used to help shape the magnetic flux into the desired pattern within the solution volume.

When the magnetic field pattern is applied to the sample solution 82, the magnetic carrier particles 80 experience forces which cause them to move toward the finger-like zones of high magnetic flux in the solution. The speed and extent to which the concentration of particles rises within these zones depends on the magnetic field strength and gradient acting on the particles 80, their size, the solution viscosity and the length of time during which the field is applied. This preferential localization of antibody-coated carrier particles due to magnetic fields forms the essential feature of the first form of the fourth embodiment shown in FIG. 8(a). The resulting localization of the particles 80 is shown in FIG. 8(a).

As a result of the sequestering of the magnetic particles 80 in these predetermined regions in the solution 82, clearly the majority of labeled antigen molecules which become bound to antibody are found within these high flux "channels" in solution. The remaining unbound labeled molecules plus any background impurities which fluoresce are unaffected by the applied field and therefore are located randomly throughout the sample volume. The resulting pattern of labeled complexes can now be detected using any of the schemes discussed earlier. It should be appreciated that a complete sequestering or localization of the magnetic carrier particles 80 within the regions of high magnetic flux is not required for successful measurement of the bound labels. The detection schemes previously discussed are in general capable of extracting a particular frequency component or temporal correlation in the overall signal whose amplitude is very small relative to the size of the overall signal, most of which may consist of baseline due to labeled molecules distributed uniformly throughout the sample volume. Depending on the detailed nature of the magnetic flux pattern, the magnetic carrier particles tend either to rather uniformly fill the high flux zones or to be distributed inhomogeneously within those regions. However, the assay technique can be made to function regardless of the form of particle localization. The carrier particles 80, themselves may give rise to a periodic signal during the scanning but this signal could be determined at the beginning of the reaction and substracted from subsequent signals.

Because the spatial pattern of labeled bound complexes as shown in FIG. 8(a) is solely the result of the application of an appropriate external magnetic field, clearly the pattern can be made to appear or disappear or to generally move throughout the assay solution 82 by judicious manipulation of the applied field. For example, simple translation of the zones of high magnetic flux shown in FIG. 8(a) can be easily accomplished, for example, by mechanical translation of an external array of magnets 86 when formed by permanent magnets. Alternatively, the flux pattern can be moved when the magnets 86 are formed as a set of electromagnets, whose windings are energized by a temporal sequence of currents designed to produce a "phased array" of fields, with the net result that the zones of high magnetic flux can be made to move spatially (i.e. translate or rotate) in discrete increments of distance, without the necessity of physical movement.

The fact that the pattern of localization of the magnetic carrier particles 80 can be caused to move within the solution 82 conveys at least two advantages to this assay method. First, there is a greater flexibility and ease in designing the pattern scanning system needed to extract the bound-label signal. In the case of fluorescent labeling, for example, the pattern can be reciprocated back and forth electrically, requiring no mechanical motion, with the result that no moving parts are required and minimal requirements for alignment of optical components. Second, the fact that the magnetic carrier particles 80 can be moved back and forth through the assay solution effectively eliminates the need for gross stirring or agitation of the solution, normally required to insure the adequate exposure of all free molecules to the surface-bound antibody. In the present embodiment, translation of the magnetic carrier particles 80 serves to bring the coated antibody into efficient contact with the antigen and labeled antigen throughout the assay solution 82. This feature should ultimately speed up the binding reaction and reduce the overall time needed to perform a homogeneous rate determination. Given the fact that active coated surfaces are not required, the fourth embodiment offers the potential advantages of ease of manufacturing of the apparatus and elimination of potentially troublesome periodic false signals due to surface-related imperfections.

It should be understood that the geometry shown in FIG. 8(a) can be modified considerably. For example, the magnetic flux pattern may be radially configured, so as to resemble the fixed pattern of the second embodiment, in which case the pattern would be rotated in time rather than translated in reciprocating fashion. The pattern could consist of just two stripes, so that on alternate cycles the magnetic particles preferentially reside either in one half of the sample solution or the adjoining half. Rather than using ferromagnetic particles one may instead choose to use paramagnetic particles.

Figure 8B:
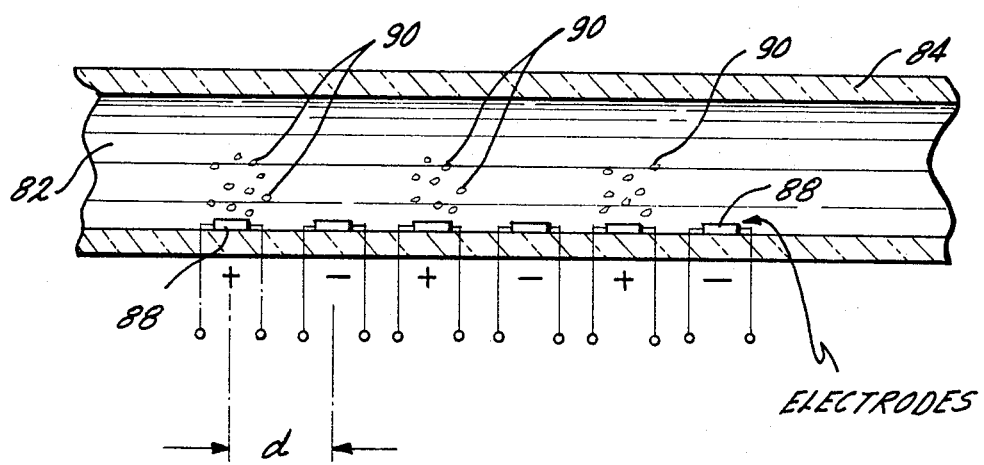

Other kinds of externally applied force fields can as well be utilized to set up a spatial pattern of labeled bound complexes within the bulk assay solution 82 without the requirement of an active surface pattern. For example, an arrangement of electrodes 88 in contact with the assay solution 82 can be used to spatially translate charged molecules and/or charged carrier particles 90 in the solution as shown in FIG. 8(b). The direction of translation depends on the sign of the charge and the speed of motion depends on the amount of charge and the friction factor, in turn related to the size of the particle 90. If a charged carrier particle 90 is used whose charge is of opposite sign to that of the unbound labeled molecules, then the bound complexes can be spatially separated from the free labels and a spatial pattern set up in solution. By comparing, for example, the signal obtained from the pattern to that obtained in the absence of the pattern (i.e. with the applied electric field first turned on, and then off), the amount of bound label can be inferred. If the charge states and resulting mobilities of the free labeled antigen and the labeled antigen-antibody complexes are sufficiently different, two species may be displaced with an applied electric field, thereby setting up a spatial pattern, without the use of carrier particles, which would be advantageous.

One could also use carrier particles 90 which are electrically polarizable instead of charged. The applied electric field would induce a dipole moment in the carrier particle 90 and the gradient of the electric field would then exert a force on the particle so that the carrier particle could be made to form a predetermined pattern in the solution 82.

It is also important to appreciate that the pattern employed need not be spatially regular. Through the use of a computer and signal averaging/enhancing techniques, some specific, non-periodic pattern may be detected. In fact, the pattern method may be used to replace the standard latex agglutination slide test now used for pregnancy testing, as discussed above. The binding of carrier particles onto a specific pattern may be detected with the eye since the human visual system is excellent in being able to detect non-random patterns or shapes in relatively noisy background environments. The sensitivity associated with the apparatus and method of the present invention is better than that which can be achieved when only random agglutination of the carrier particles is the event which is to be recognized. Multiple assays could then be performed by using a set of patterns which are deposited on a surface in the form of different alphabet letters, numbers or other simple geometric shapes whose identification would be relatively unambiguous.

It is also important to appreciate that all of the techniques associated with the formation of spatial patterns described herein can be used to assay whole cells. Here, for example, one may wish to detect the concentration of certain antigens located on the cell surface or to determine the fraction of cells which contain a given molecule on their cell surface. In this case, the antigen-antibody complexes consist of cells bound to the antibody-coated pattern segments.

Although the present invention has been described with reference to particular embodiments, it is to be appreciated that various adaptations and modifications may be made and the invention is only to be limited to the appended claims.

We claim:

1. Apparatus for providing an immunoassay of a binding reaction between an ligand and an antiligand, including
    a spatial pattern formed by a predetermined known spatially periodic array of stripes of antiligand material and with the stripes having a predetermined width and spacing,
    ligand material dispersed to interact with the spatially periodic array of stripes of antiligand material for producing a binding reaction between the ligand and the antiligand in the spatial pattern of stripes,
    means for labeling the binding reaction with a particular physical characteristic,
    a source of input energy and with the input energy at a particular spectrum for interacting with the particular physical characteristic of the labeled binding reaction,
    means for scanning the spatial pattern with the input energy at the particular spectrum for producing output energy having amplitude levels formed by a substantially random background component and a periodic component representing the labeled binding reaction, and
    means responsive to the output energy for detecting the periodic component representing the labeled binding reaction and for producing an output signal in accordance with the labeled binding reaction.

2. The apparatus for providing an immunoassay of claim 1 additionally including a cylindrical member and with the spatial pattern formed as a plurality of vertical stripes arranged circumferentially around the cylindrical member.

3. The apparatus for providing an immunoassay of claim 2 wherein the plurality of vertical stripes are on the inside surface of the cylindrical member and the ligand material is dispersed in a liquid contained within the cylindrical member.

4. The apparatus for providing an immunoassay of claim 2 wherein the means for scanning includes means for rotating the cylindrical member while the input energy is directed toward the spatial pattern.

5. The apparatus for providing an immunoassay of claim 1 additionally including a disc member and with the spatial pattern formed as a plurality of radial stripes arranged around a center point of the disc.

6. The apparatus for providing an immunoassay of claim 5 wherein the radial stripes are on a top surface of the disc and the ligand material is dispersed in a layer of liquid on the top surface of the disc.

7. The apparatus for providing an immunoassay of claim 5 wherein the means for scanning includes rotating the disc member while the input energy is directed toward the spatial pattern.

8. The apparatus for providing an immunoassay of claim 1 additionally including a substantially flat member and with the spatial pattern formed as a plurality of horizontal stripes arranged across the flat member.

9. The apparatus for providing an immunoassay of claim 8 wherein the horizontal stripes are on a top surface of the flat member and the ligand material is dispersed in a layer of liquid on the top surface of the flat member.

10. The apparatus for providing an immunoassay of claim 8 wherein the means for scanning includes scanning the input energy back and forth across the flat member in a direction perpendicular to the horizontal stripes.

11. The apparatus for providing an immunoassay of claim 1 wherein the labeled binding reaction between the ligand and antiligand is performed as a competitive assay including a known labeled ligand and an unknown unlabeled ligand both interacting with the antiligand to produce the binding reaction.

12. The apparatus for providing an immunoassay of claim 11 wherein the ligand to be labeled is attached to labeled carrier particles.

13. The apparatus for providing an immunoassay of claim 1 wherein the labeled binding reaction between the ligand and antiligand is performed as a sandwich assay including a known labeled antiligand and a known unlabeled antiligand and with an initial binding reaction between the ligand and the known unlabeled antiligand of a quantity sufficient to bind substantially all of the ligand and with a subsequent binding reaction between the known labeled antiligand and the product of the initial binding reaction.

14. The apparatus for providing an immunoassay of claim 13 wherein the antiligand to be labeled is attached to labeled carrier particles.

15. The apparatus for providing an immunoassay of claim 1 wherein the labeling of the binding reaction is a fluorescent label.

16. The apparatus for providing an immunoassay of claim 1 wherein the means for scanning includes moving the spatial pattern while the input energy is directed toward the moving spatial pattern.

17. The apparatus for providing an immunoassay of claim 1 wherein the means for scanning includes maintaining the spatial pattern stationary while scanning the input energy across the stationary spatial pattern.

18. The apparatus for providing an immunoassay of claim 1 wherein the means for detecting includes an electronic filter having a frequency range for passing the periodic component while discriminating against the random background component.

19. The apparatus for providing an immunoassay of claim 1 wherein the detecting includes a phase-lock detector for amplifying the periodic component while discriminating against the background component.

20. The apparatus for providing an immunoassay of claim 1 wherein the means for detecting includes an autocorrelator for extracting the periodic component from the random background component.

21. The apparatus for providing an immunoassay of claim 1 where the antiligand is attached to carrier particles and the periodic pattern is formed by a spatially periodic force field to which the carrier particles are responsive.

22. The apparatus for providing an immunoassay of claim 21 wherein the carrier particle is magnetic and the force field is a magnetic field.

23. The apparatus for providing an immunoassay of claim 21 wherein the carrier particle is electrically charged and the force field is an electric field.

24. The apparatus for providing an immunoassay of claim 21 wherein the carrier particle is electrically polarizable and the force field is an electric field.

25. Apparatus for providing an immunoassay of a binding reaction between a ligand and an antiligand, including
a spatial pattern formed by a predetermined known spatial array of separate areas of antiligand material,
ligand material dispersed to interact with the spatial array of separate areas of antiligand material for producing a binding reaction between the ligand and the antiligand in the spatial pattern,
means for labeling the binding reaction with a particular physical characteristic,
a source of input energy and with the input energy at a particular spectrum for interacting with the particular physical characteristic of the labeled binding reaction,
means for scanning the spatial pattern with the input energy at the particular spectrum for producing output energy having amplitude levels formed by a substantially random background component and a non-random component representing the labeled binding reaction, and
means responsive to the output energy for detecting the non-random component representing the labeled binding reaction and for producing an output signal in accordance with the labeled binding reaction.

26. The apparatus for providing an immunoassay of claim 25 additionally including a cylindrical member and with the spatial pattern formed as a plurality of vertical areas arranged circumferentially around the cylindrical member.

27. The apparatus for providing an immunoassay of claim 26 wherein the plurality of vertical areas are on the inside surface of the cylindrical member and the antigen material is dispersed in a liquid contained within the cylindrical member.

28. The apparatus for providing an immunoassay of claim 26 wherein the means for scanning includes means for rotating the cylindrical member while the input energy is directed toward the spatial pattern.

29. The apparatus for providing an immunoassay of claim 25 additionally including a disc member and with the spatial pattern formed as a plurality of radial areas arranged around a center point of the disc.

30. The apparatus for providing an immunoassay of claim 29 wherein the radial areas are on a top surface of the disc and the antigen material is dispersed in a layer of liquid on the top surface of the disc.

31. The apparatus for providing an immunoassay of claim 29 wherein the means for scanning includes rotating the disc member while the input energy is directed toward the spatial pattern.

32. The apparatus for providing an immunoassay of claim 25 additionally including a substantially flat member and with the spatial pattern formed as a plurality of horizontal areas arranged across the flat member.

33. The apparatus for providing an immunoassay of claim 32 wherein the horizontal areas are on a top surface of the flat member and the ligand material is dispersed in a layer of liquid on the top surface of the flat member.

34. The apparatus for providing an immunoassay of claim 32 wherein the means for scanning includes scanning the input energy back and forth across the flat member in a direction perpendicular to the horizontal stripes.

35. The apparatus for providing an immunoassay of claim 25 wherein the labeled binding reaction between the ligand and antiligand is performed as a competitive assay including a known labeled ligand and an unknown unlabeled ligand both interacting with the antiligand to produce the binding reaction.

36. The apparatus for providing an immunoassay of claim 35 wherein the ligand to be labeled is attached to labeled carrier particles.

37. The apparatus for providing an immunoassay of claim 25 wherein the labeled binding reaction between the ligand and antiligand is performed as a sandwich assay including a known labeled antiligand and a known unlabeled antiligand and with an initial binding reaction between the ligand and the known unlabeled antiligand of a quantity sufficient to bind all of the ligand and with a subsequent binding reaction between the known labeled antiligand and the product of the initial binding reaction.

38. The apparatus for providing an immunoassay of claim 37 wherein the antiligand to be labeled is attached to labeled carrier particles.

39. The apparatus for providing an immunoassay of claim 25 wherein the labeling of the binding reaction is a fluorescent label.

40. The apparatus for providing an immunoassay of claim 25 wherein the means for scanning includes moving the spatial pattern while the input energy is directed toward the moving spatial pattern.

41. The apparatus for providing an immunoassay of claim 25 wherein the means for scanning includes maintaining the spatial pattern stationary while scanning the input energy across the stationary spatial pattern.

42. The apparatus for providing an immunoassay of claim 25 wherein the means for detecting includes a filter having a frequency range for passing the non-random component while discriminating against the random background component.

43. The apparatus for providing an immunoassay of claim 25 wherein the means for detecting includes a phase lock detector for amplifying the non-random component while discriminating against the random background component.

44. The apparatus for providing an immunoassay of claim 25 wherein the means for detecting includes an autocorrelator for extracting the non-random component from the random background component.

45. The apparatus for providing an immunoassay of claim 25 where the antiligand is attached to carrier particles and the spatial pattern is formed by a spatial force field to which the carrier particles are responsive.

46. The apparatus for providing an immunoassay of claim 45 wherein the carrier particle is magnetic and the force field is a magnetic field.

47. The apparatus for providing an immunoassay of claim 45 wherein the carrier particle is electrically charged and the force field is an electric field.

48. The apparatus for providing an immunoassay of claim 45 wherein the carrier is electrically polarizable and the force field is an electric field.

49. A method for providing an immunoassay of a binding reaction between a ligand and an antiligand including the following steps,
   providing a spatial pattern formed by a predetermined known spatial array of separate areas of antiligand material,
   providing a ligand material dispersed to interact with the spatial array of separate areas of antiligand material for producing a binding reaction between the ligand and the antiligand in the spatial pattern,
   labeling the binding reaction with a particular physical characteristic,
   providing input energy at a particular spectrum for interacting with the paticular physical characteristic of the labeled binding reaction,
   scanning the spatial pattern with the input energy at the particular spectrum for producing output energy having amplitude levels formed by a substantially random background component and a non-random component representing the labeled binding reaction, and
   detecting the non-random component representing the labeled binding reaction and for producing an output signal in accordance with the labeled binding reaction.

50. The method of claim 49 wherein the spatial pattern is formed as a plurality of vertical areas arranged circumferentially around a cylindrical member.

51. The method of claim 50 wherein the plurality of vertical areas are on the inside surface of the cylindrical member and the antigen material is dispersed in a liquid contained within the cylindrical member.

52. The method of claim 50 wherein the scanning includes rotating the cylindrical member while the input energy is directed toward the spatial pattern.

53. The method of claim 49 wherein the spatial pattern is formed as a plurality of radial areas arranged around a center point of the disc.

54. The method of claim 53 wherein the radial areas are on a top surface of the disc and the antigen material is dispersed in a layer of liquid on the top surface of the disc.

55. The method of claim 53 wherein the scanning includes rotating the disc member while the input energy is directed toward the spatial pattern.

56. The method of claim 49 wherein the spatial pattern is formed as a plurality of horizontal areas arranged across the flat member.

57. The method of claim 56 wherein the horizontal areas are on a top surface of the flat member and the ligand material is dispersed in a layer of liquid on the top surface of the flat member.

58. The method of claim 56 wherein the scanning includes scanning the input energy back and forth across the flat member in a direction perpendicular to the horizontal stripes.

59. The method of claim 49 wherein the labeled binding reaction between the ligand and antiligand is performed as a competitive assay including a known labeled ligand and an unknown unlabeled ligand both interacting with the antiligand to the binding reaction.

60. The method of claim 59 wherein the ligand to be labeled is attached to labeled carrier particles.

61. The method of claim 49 wherein the labeled binding reaction between the ligand and antiligand is performed as a sandwich assay including a known labeled antiligand and a known unlabeled antiligand and with an initial binding reaction between the ligand and the known unlabeled antiligand of a quantity sufficient to bind all of the ligand and with a subsequent binding reaction betwen the known labeled antiligand and the product of the initial binding reaction.

62. The method of claim 61 wherein the antiligand to be labeled is attached to labeled carrier particles.

63. The method of claim 49 wherein the labeling of the binding reaction is a fluorescent label.

64. The method of claim 49 wherein the scanning includes moving the spatial pattern while the input energy is directed toward the moving spatial pattern.

65. The method of claim 49 wherein the scanning includes maintaining the spatial pattern stationary while scanning the input energy across the stationary spatial pattern.

66. The method of claim 49 wherein the detecting includes filtering with a frequency range for passing the non-random component while discriminationg against the random background component.

67. The method of claim 49 wherein the detecting includes phase-lock detecting by amplifying the non-random component while discriminating against the random background component.

* * * * *